United States Patent
Brandl et al.

(10) Patent No.: US 6,450,962 B1
(45) Date of Patent: Sep. 17, 2002

(54) ULTRASONIC DIAGNOSTIC METHODS AND APPARATUS FOR GENERATING IMAGES FROM MULTIPLE 2D SLICES

(75) Inventors: Helmut Brandl, Pfaffing; Josef Steininger, Vocklamarkt; Arthur Gritzky, Pollham, all of (AT)

(73) Assignee: Kretztechnik AG, Zipf (AT)

( * ) Notice: Subject to any disclaimer, the term of this patent is extended or adjusted under 35 U.S.C. 154(b) by 0 days.

(21) Appl. No.: 09/954,805

(22) Filed: Sep. 18, 2001

(51) Int. Cl.[7] ................................................ A61B 8/14
(52) U.S. Cl. ...................... 600/458; 600/447; 600/443; 600/441; 600/440
(58) Field of Search .............................. 600/458, 447, 600/440, 437, 443, 441; 348/441; 345/419; 128/916

(56) References Cited

U.S. PATENT DOCUMENTS

| | | | | |
|---|---|---|---|---|
| 5,787,889 A | * | 8/1998 | Edwards et al. | 128/916 |
| 5,911,691 A | * | 6/1999 | Mochizuki et al. | 128/916 |
| 5,986,662 A | * | 11/1999 | Argiro et al. | 345/419 |
| 6,106,471 A | * | 8/2000 | Wiesauer et al. | 600/443 |
| 6,186,949 B1 | * | 2/2001 | Hatfield et al. | 128/916 |
| 6,201,900 B1 | * | 3/2001 | Hossack et al. | 348/441 |
| 6,213,947 B1 | * | 4/2001 | Phillips | 600/443 |
| 6,254,540 B1 | * | 7/2001 | Kikuchi et al. | 600/443 |
| 6,283,918 B1 | * | 9/2001 | Kanda et al. | 128/916 |

OTHER PUBLICATIONS

Jean–Louis Coatrieux and Christian Barillot, A Survey of 3D Display Techniqes to Render Medical Data, published in 3D Imaging in Medicine: Algorithms, Systems, Applications, Karl Heinz Hohne et al. editors, Springer–Verlag, Berlin Heidelberg, NATO ASI Series F: Computer and Systems Sciences, vol. 60, pp. 175–195 (1990).

Karl Heinz Hohne et al., Rendering Tomographic Volume Data: Adequacy of Methods for Different Modalities and Organs, published in 3D Imaging in Medicine: Algorithms, Systems, Applications, Karl Heinz Hohne et al. editors, Springer–Verlag, Berlin Heidelberg, NATA ASI Series F: Computer and Systems Sciences, vol. 60, pp. 197–215 (1990).

\* cited by examiner

*Primary Examiner*—Marvin M. Lateef
*Assistant Examiner*—Ruby Jain
(74) *Attorney, Agent, or Firm*—McAndrews, Held & Malloy, Ltd.; Peter J. Vogel; Michael A. Dellapenna

(57) ABSTRACT

A method and systems for obtaining 2D ultrasound images. The methods may comprise the steps of receiving ultrasonic information from a volumetric region of a body, volume scan converting the ultrasonic information from the volumetric region for processing a rendering box, and volume rendering the rendering box for projecting the rendering box onto a 2D slice by using volume rendering techniques. The systems may comprise an ultrasonic transducer for receiving ultrasonic information from a volumetric region of a body, a volume scan converter for processing a rendering box obtained from the volumetric region, and a volume rendering processor for projecting the rendering box onto a 2D slice by using volume rendering techniques for contrast enhancement.

32 Claims, 2 Drawing Sheets

ULTRASONIC DIAGNOSTIC METHODS AND APPARATUS FOR GENERATING IMAGES FROM MULTIPLE 2D SLICES

BACKGROUND OF THE INVENTION

Embodiments of the present invention are directed generally to ultrasonic imaging. More particularly, various embodiments of the present invention are directed to apparatus and methods for generating 2D images from multiple 2D slices at different spatial locations.

Conventional 2D ultrasound scanners produce a two-dimensional slice by using a transducer to transmit ultrasonic pulses and receive echoes from structures inside a body. While the transducer is held in one position, pulses are fired to multiple points throughout a 2D scan area. The scan area is formed in a single plane and has a very thin thickness. The echo information is then displayed as a planar image made up of 2D pixels. The displayed information depends on specific properties of the transducer such as frequency, focal range, and axial and lateral resolution. While certain properties of the transducer can be varied (e.g., transmission frequency, receive frequency), it remains desirable to improve image quality by improving tissue contrast in conventional 2D images. Thus, there is a need for methods and apparatus of ultrasound imaging that continue to improve tissue contrast.

Two conventional methods of contrast enhancement concern filtering and utilizing a dynamic window. The filtering and windowing methods may decrease the amount of information in the image because of the presence of speckle. Thus, there is a need for methods and apparatus of ultrasound imaging that improve tissue contrast by reducing speckle.

BRIEF SUMMARY OF THE INVENTION

In accordance with one embodiment of the present invention, a medical diagnostic ultrasound system for developing a 2D image having contrast enhancement comprises an ultrasonic transducer for receiving ultrasonic information from a volumetric region of a body, memory storing adjacent image lines or planes formed from received ultrasonic information from the volumetric region, a rendering box control module defining a thickness of a rendering box overlapping a portion of the adjacent image lines or planes, and a volume rendering processor for combining and projecting portions of image lines or planes within the rendering box onto a 2D image based on volume rendering techniques that enhance contrast.

The ultrasonic transducer may be a 3D transducer or a 2D matrix array. The system may further comprise a volume scan converter that generates the image lines or planes based on geometric information that calculates a position of neighboring ultrasonic information to derive voxel data. The volume rendering processor may project the portion of the image lines or planes in the rendering box in real-time. The system may further comprise memory for storing the ultrasonic information before being scan converted to form the image lines or planes. The volume rendering processor may employ algorithms for surface texture and maximum transparency. The volume rendering processor may perform at least one of the following operations upon the image lines or planes: surface texture, maximum transparency, transparent minimum, and gradient light rendering. The transducer may operate in at least one of the following acquisition modes: conventional grayscale sonography, 2D compound imaging, color Doppler, and duplex sonography with spectral Doppler. The transducer may receive tissue harmonic imaging information. The transducer may receive pulse inversion harmonic imaging information.

Certain embodiments of the present invention comprise a method for developing a 2D image representation for image contrast enhancement in a medical diagnostic ultrasound system comprising the steps of: receiving ultrasonic information from a volumetric region of a body, storing adjacent image lines or planes formed from received ultrasonic information from the volumetric region, forming a rendering box overlapping a portion of the adjacent image lines or planes and having a thickness, and volume rendering the rendering box for combining and projecting portions of image lines or planes within the rendering box onto a 2D image based on volume rendering techniques that enhance contrast.

The step of receiving ultrasonic information may be performed by a 3D transducer or a 2D matrix array. The method may further comprise a step of volume scan converting that generates the image lines or planes based on geometric information that calculates a position of neighboring ultrasonic information to derive voxel data. The step of volume rendering may project the portion of the image lines or planes in the rendering box in real-time. The method may further comprise a step of storing the ultrasonic information before being scan converted to form the image lines or planes. The step of volume rendering may perform at least one of the following operations upon the image lines or planes: surface texture, maximum transparency, transparent minimum, and gradient light rendering. The step of receiving ultrasonic information may employ at least one of the following acquisition modes: conventional grayscale sonography, 2D compound imaging, color Doppler, and duplex sonography with spectral Doppler. The step of receiving ultrasonic information may comprise receiving tissue harmonic imaging information. The step of receiving ultrasonic information may comprise receiving pulse inversion harmonic imaging information.

BRIEF DESCRIPTION OF THE DRAWINGS

The foregoing summary, as well as the following detailed description of the preferred embodiments of the present invention, will be better understood when read in conjunction with the appended drawings. For the purpose of illustrating the preferred embodiments of the present invention, there is shown in the drawings, embodiments which are presently preferred. It should be understood, however, that the present invention is not limited to the arrangements and instrumentality shown in the attached drawings.

DETAILED DESCRIPTION OF THE INVENTION

Figure 1:
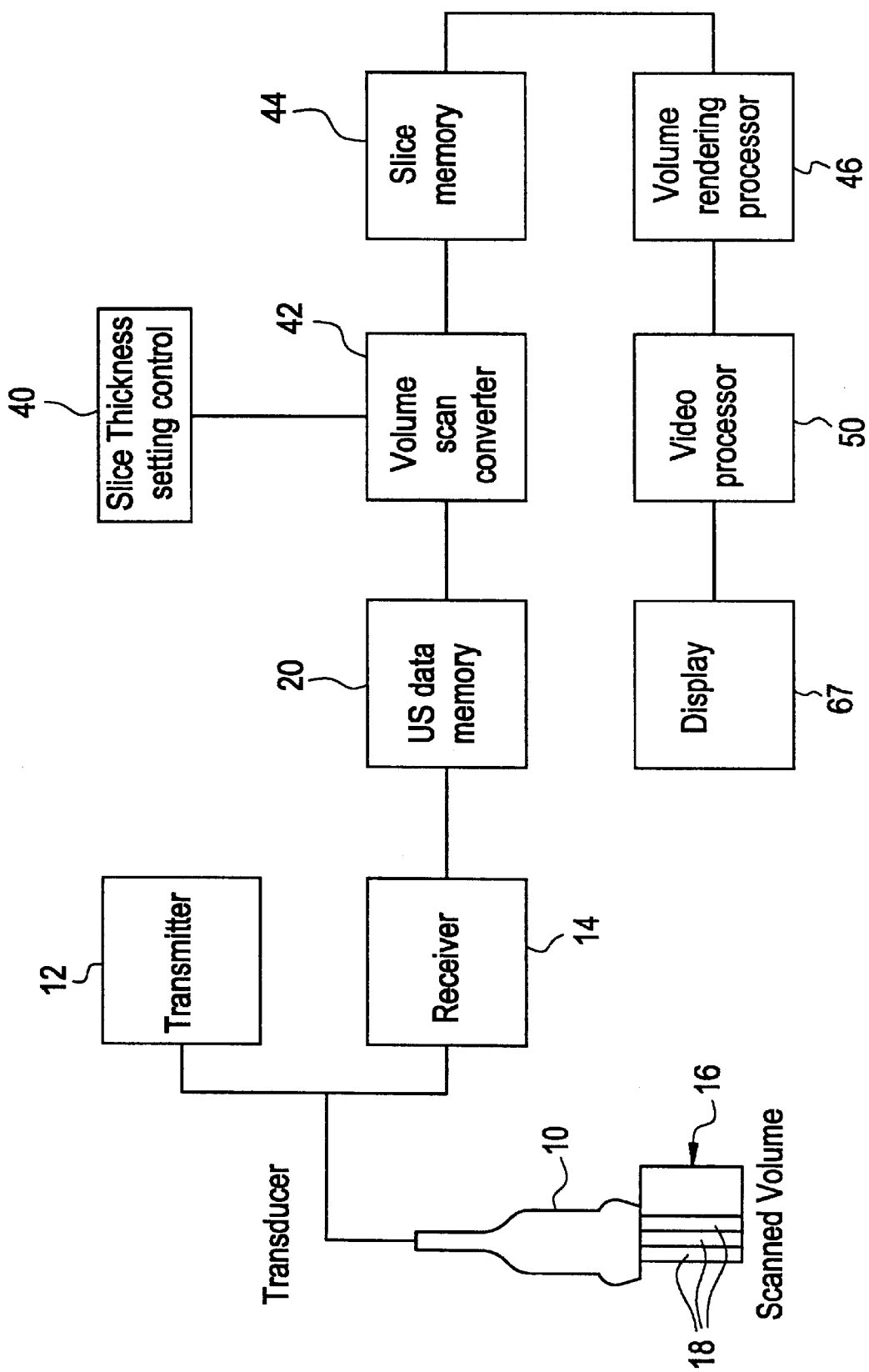
FIG. 1 is a block diagram of an apparatus formed in accordance with one embodiment of the present invention.

FIG. 1 illustrates an ultrasound system formed in accordance with one embodiment of the present invention. The system includes a probe 10 connected to a transmitter 12 and a receiver 14. The probe 10 transmits ultrasonic pulses and receives echoes from structures inside of a scanned ultrasound volume 16. Memory 20 stores ultrasound data from the receiver 14 derived from the scanned ultrasound volume 16. The volume 16 may be obtained by various techniques (e.g., 3D scanning, real-time 3D imaging, volume scanning, 2D scanning with transducers having positioning sensors, freehand scanning using a Voxel correlation technique, 2D or matrix array transducers and the like).

The transducer 10 is moved, such as along a linear or arcuate path, while scanning a region of interest (ROI). At each linear or arcuate position, the transducer 10 obtains scan planes 18. The scan planes 18 are collected for a thickness, such as from a group or set of adjacent scan planes 18. The scan planes 18 are stored in the memory 20, and then passed to a volume scan converter 42. In some embodiments, the transducer 10 may obtain lines instead of the scan planes 18, and the memory 20 may store lines obtained by the transducer 10 rather than the scan planes 18. The volume scan converter 42 receives a slice thickness setting from a control input 40, which identifies the thickness of a slice to be created from the scan planes 18. The volume scan converter 42 creates a data slice from multiple adjacent scan planes 18. The number of adjacent scan planes 18 that are combined to form each data slice is dependent upon the thickness selected by slice thickness control input 40. The data slice is stored in slice memory 44 and is accessed by a volume rendering processor 46. The volume rendering processor 46 performs volume rendering upon the data slice. The output of the volume rendering processor 46 is passed to the video processor 50 and display 67.

The position of each echo signal sample (Voxel) is defined in terms of geometrical accuracy (i.e., the distance from one Voxel neighbor to the next) and ultrasonic response (and derived values from the ultrasonic response). Suitable ultrasonic responses include gray scale values, color flow values, and angio or power Doppler information.

Figure 2:
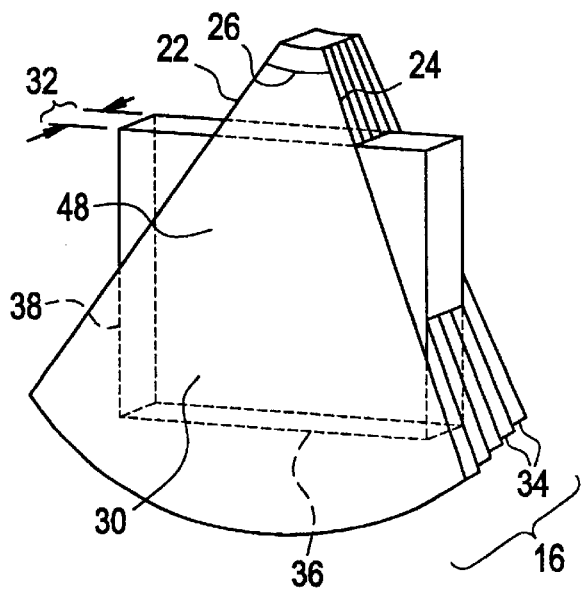
FIG. 2 is an isometric drawing of a rendering box formed in accordance with one embodiment of the present invention.

FIG. 2 illustrates a real-time 4D volume 16 acquired by the system of FIG. 1 in accordance with one embodiment. The volume 16 includes a sector shaped cross-section with radial borders 22 and 24 diverging from one another at angle 26. The probe 10 electronically focuses and directs ultrasound firings longitudinally to scan along adjacent scan lines in each scan plane 18 and electronically or mechanically focuses and directs ultrasound firings laterally to scan adjacent scan planes 18. Scan planes 18 obtained by the probe 10, as illustrated in FIG. 1, are stored in memory 20 and are scan converted from spherical to Cartesian coordinates by the volume scan converter 42. A volume comprising multiple scan planes is output from the volume scan converter 42 and stored in the slice memory 44 as rendering box 30 (FIG. 2). The rendering box 30 in the slice memory 44 is formed from multiple adjacent image planes 34.

The rendering box 30 may be defined in size by an operator to have a slice thickness 32, width 36 and height 38. The volume scan converter 42 may be controlled by the slice thickness control input 40 to adjust the thickness parameter of the slice to form a rendering box 30 of the desired thickness. The rendering box 30 designates the portion of the scanned volume 16 that is volume rendered. The volume rendering processor 46 accesses the slice memory 44 and renders along the thickness 32 of the rendering box 30.

During operation, a 3D slice having a pre-defined, substantially constant thickness (also referred to as the rendering box 30) is acquired by the slice thickness setting control 40 (FIG. 1) and is processed in the volume scan converter 42 (FIG. 1). The echo data representing the rendering box 30 may be stored in slice memory 44. Predefined thicknesses between 2 mm and 20 mm are typical, however, thicknesses less than 2 mm or greater than 20 mm may also be suitable depending on the application and the size of the area to be scanned. The slice thickness setting control 40 may include a rotatable knob with discrete or continuous thickness settings.

The volume rendering processor 46 projects the rendering box 30 onto an image portion 48 of an image plane 34 (FIG. 2). Following processing in the volume rendering processor 46, the pixel data in the image portion 48 may pass through a video processor 50 and then to a display 67.

The rendering box 30 may be located at any position and oriented at any direction within the scanned volume 16. In some situations, depending on the size of the region being scanned, it may be advantageous for the rendering box 30 to be only a small portion of the scanned volume 16.

Once the rendering box 30 is placed over the scanned volume 16, the volume rendering processor 46 performs a projection operation through the rendering box 30 to combine Voxels in adjacent image planes 34. The adjacent Voxels are combined to form a single 2D rendered image. The Voxels to be combined are determined by the desired view and projection angle. For example, if a view is desired orthogonal to the rendering box 30, the rendering process combines Voxels arranged along lines or rays extending perpendicular to, and through, the image planes 34.

While the direction of projection onto the image portion 48 may be orthogonal to the center image plane 34, it need not be orthogonal. For example, at relatively small scan angles 26, the image planes 34 may not be parallel to one another, nor parallel to a reference coordinate system in which the image planes 34 are stored. Hence, if the rendering box 30 is parallel to the reference coordinate system, projection may occur at an angle to the image planes 34 and, in such a case, the direction of projection onto the image portion 48 is not orthogonal. Alternatively, the rendering box 30 may be defined at an angle to the reference coordinate system.

The scanned volume 16 may include a number of scan lines that have inconstant resolution. A reason for inconstant resolution is that when ultrasound echo beams are received, the echo beams vary in thickness along their length as a result of being out of focus at certain depths and in focus at other depths. The error of inconstant resolution may be reduced by a pre-defined constant thickness at the slice thickness setting control 40. Increases in thickness generally reduce the error of inconstant resolution. The rendering box 30 need not have a pre-defined constant thickness.

The volume rendering processor 46 may perform several different filtering algorithms, such as averaging, median filtering, and the like between adjacent pixels in one image plane 34. The volume rendering algorithms employed in connection with certain embodiments of the present invention increase the contrast of soft tissue (i.e., improve tissue differentiation). The amount of tissue differentiation depends on the selected pre-defined slice thickness, and on the object scanned. Typically, thicker slices result in higher contrast.

The volume rendering algorithms used in accordance with certain embodiments of the present invention to combine adjacent image planes 34 include the following general types: maximum intensity projection, minimum intensity projection, and surface rendering using fuzzy segmentation in combination with either the voxel texture information, the depth information, gradient shading and the like. Various particular rendering algorithms are described in detail in the book 3D Imaging in Medicine; Algorithms, Systems, Applications; Edited by Karl Heinz Hohne, Henry Fuchs, Stephen M. Pizer; NATO ASI Series; Springer Verlag 1990, which is hereby incorporated by reference. Combination of rendering algorithms can be applied in the volume rendering processor 46.

The volume rendering algorithms may operate on relatively thin slices or thin rendering boxes 30 to improve the tissue contrast. When imaging some relatively small patient areas, taking a relatively thick rendering box 30 may cause a loss of information. For example, an operator may take a relatively thin rendering box 30 of a small tumor to avoid loss of information, whereas a relatively thick rendering box 30 may be taken of an organ such as a kidney to provide a significant improvement in contrast resolution of the large organ. Applying the volume rendering algorithms to relatively thin rendering box 30 results in an improvement of contrast of a B-image, particularly in small scanned volumes 16.

In one embodiment, a real-time display of a region of interest results from a rendering mode that comprises a mixture of surface texture and transparent maximum rendering modes. The real-time display may give a physician more flexibility when diagnosing the region. In an alternative embodiment in which the rendering mode comprises a mixture of surface texture and transparent maximum rendering modes, the display is not real-time. Various ratios of surface texture and transparent maximum rendering modes may be employed on the rendering box 30. For example, the final 2D image may comprise 60% of the gray value of the surface texture image plus 40% of the gray value of the transparent maximum image. Ratios other than 60%/40% are also suitable and include 80%/120%, 75%/25%, and 70%/30%. Other ratios may be applied. Surface texture and transparent maximum rendering modes result in less speckle pattern and a highly improved tissue contrast (i.e., the signal/noise ratio is improved). The improved tissue contrast facilitates the finding of diffuse lesions in organs.

Embodiments in which volume rendering algorithms are employed on relatively thin rendering boxes 30 to improve the tissue contrast can be used for the following 3D or 3D real-time (4D) acquisition modes or combinations of the following 3D or 3D real-time (4D) acquisition modes: conventional grayscale sonography, 2D compound imaging, tissue harmonic imaging, pulse inversion harmonic imaging, duplex sonography with color flow mapping (CFM), duplex sonography with power Doppler, or duplex sonography with spectral Doppler.

Figure 3:
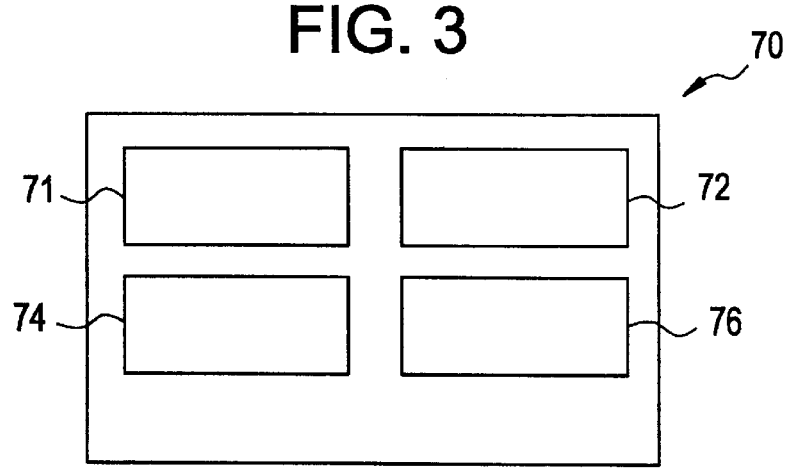
FIG. 3 is a schematic of an ultrasound display that displays an example of an embodiment of volume rendering imaging in accordance with one embodiment of the present invention.

For the projection of a 3D rendering box 30 onto the display 67, another embodiment of the present invention performs rendering in real-time 4D scanning, using a multi-planar display mode. A display 70 having multi-planar display mode is shown in FIG. 3. For ease of description, all four images in the display 70 are shown schematically. Multi-planar display mode enables an operator to see the B-image that is being obtained 71 (in the upper left in FIG. 3), a plane 72 orthogonal to the B-image 71 and seen in the scan direction of the transducer movement, a coronal plane 74 which is orthogonal to the planes 71 and 72, and an image 76 that has been volume rendered to enhance contrast. Real-time 4D scanning with multi-planar display is similar to the rendering of stored, static 3D volumes but is applied during 4D scanning. The projection of the rendering box 30 is made onto the coronal plane 74. However, an operator can select to project the rendering box 30 onto any of the three planes 71, 72, or 74. A large volume sweep angle 26 may be chosen by an operator to switch the plane (e.g., 71, 72, or 74) onto which the rendering box 30 will be projected. Therefore there is a lower volume rate per second. For structures which do not move (such as a breast) the lower volume rate per second is not a problem.

Figure 4:
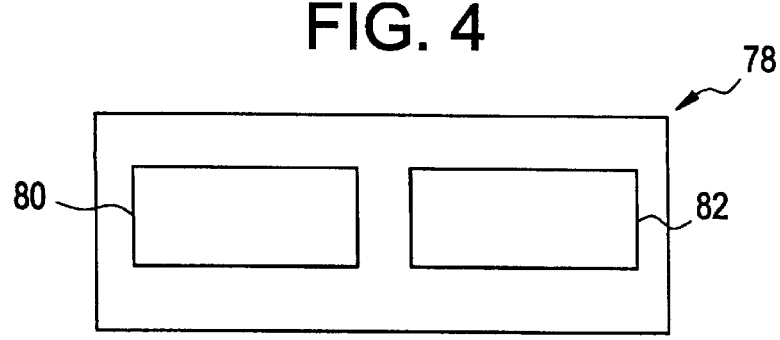
FIG. 4 is a diagram illustrating a split screen display in accordance with an embodiment of the present invention.

For the projection of the 3D rendering box 30 onto the 2D display 67, a further embodiment of the present invention performs volume rendering in real-time 4D scanning as a pseudo 2D mode. A very small volume sweep angle 26 is used. As seen in FIG. 4, a split screen 78 may be employed to show (a) a typical B-image on the plane 80 onto which volume rendering occurs and (b) an image 82 volume rendered in accordance with an embodiment of the present invention. Images 80 and 82 are shown schematically. Because of the small sweep angle 26, there is a high volume rate (displayed images per second or frame rate).

In order to project the rendering box 30 onto the display 67, some embodiments of the present invention perform rendering on stored, static 3D volumes. The process is similar to the process shown in FIG. 2 and discussed in connection with the real-time 4D volume rendering image embodiment shown in FIG. 2. First an operator selects a desired plane to be the plane onto which projection occurs. Then the operator selects a suitable thickness. Following those two steps, the rendering box 30 has been created and can be moved freely within the stored volume.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A medical diagnostic ultrasound system for developing real-time updated images having contrast enhancement, the system comprising:

an ultrasonic transducer for receiving, in real-time, ultrasonic information from a volumetric region of a body;

memory storing adjacent image lines or planes formed from said ultrasonic information received in real-time from said volumetric region;

a rendering box control module defining a thickness of a rendering box overlapping a portion of said adjacent image lines or planes; and a volume rendering processor projecting said rendering box onto portions of said adjacent image lines or planes in real-time while said ultrasonic transducer continues to receive said real-time ultrasonic information, said volume rendering processor processing said adjacent image lines or planes within said rendering box based on volume rendering techniques that enhance contrast.

2. The system of claim 1, wherein said ultrasonic transducer for receiving said real-time ultrasonic information is a 3D transducer.

3. The system of claim 1, wherein said ultrasonic transducer for receiving said real-time ultrasonic information is a 2D matrix array.

4. The system of claim 1, further comprising a volume scan converter generating said image lines or planes based on voxel correlation technique that calculates a position of neighboring ultrasonic information to derive voxel data.

5. The system of claim 1, wherein the real-time ultrasonic information from the volumetric region of the body is obtained by a 3D freehand scanning technique with positioning sensor.

6. The system of claim 1, wherein the real-time ultrasonic information from the volumetric region of the body is obtained by a 3D freehand scanning technique without positioning sensor.

7. The system of claim 1, further comprising a second memory for storing said real-time ultrasonic information before being scan converted to form said image lines or planes.

8. The system of claim 1, said volume rendering processor utilizing algorithms for surface texture and maximum transparency to process said adjacent image lines or planes within said rendering box.

9. The system of claim 1, wherein the volume rendering processor performs at least one of the following operations upon said image lines or planes: surface texture, maximum transparency, transparent minimum, and gradient light rendering.

10. The system of claim 1, wherein the ultrasonic transducer can operate in at least one of the following acquisition modes: conventional grayscale sonography, 2D compound imaging, color Doppler, and duplex sonography with spectral Doppler.

11. The system of claim 1, wherein the ultrasonic transducer receives tissue harmonic imaging information.

12. The system of claim 1, wherein the ultrasonic transducer receives pulse inversion harmonic imaging information.

13. A method for developing an image representation for image contrast enhancement in a medical diagnostic ultrasound system, said method comprising the steps of:
receiving, in real-time, ultrasonic information from a volumetric region of a body;
storing adjacent image lines or planes formed from said ultrasonic information received in real-time from said volumetric region;
forming a rendering box overlapping a portion of said adjacent image lines or planes and having a thickness;
projecting said rendering box onto said adjacent image lines or planes in real-time while said ultrasonic information is being received from the volumetric region of the body; and
volume rendering said adjacent image lines or planes within said rendering box in real-time based on volume rendering techniques that enhance contrast.

14. The method of claim 13, wherein said step of receiving real-time ultrasonic information is performed by a 3D transducer.

15. The method of claim 13, wherein said step of receiving real-time ultrasonic information is performed by a 2D matrix array.

16. The method of claim 13, further comprising a step of volume scan converting said real-time ultrasonic information to generate said image lines or planes based on a voxel correlation technique that calculates a position of neighboring ultrasonic information to derive voxel data.

17. The method of claim 13, wherein the real-time ultrasonic information from the volumetric region of the body is obtained by a 3D freehand scanning technique with positioning sensor.

18. The method of claim 13, wherein the real-time ultrasonic information from the volumetric region of the body is obtained by a 3D freehand scanning technique without positioning sensor.

19. The method of claim 13, further comprising a step of storing said real-time ultrasonic information before being scan converted to form said image lines or planes.

20. The method of claim 13, wherein the step of volume rendering performs at least one of the following operations upon said image lines or planes: surface texture, maximum transparency, transparent minimum, and gradient light rendering.

21. The method of claim 13, wherein the step of receiving real-time ultrasonic information employs at least one of the following acquisition modes: conventional grayscale sonography, 2D compound imaging, color Doppler, and duplex sonography with spectral Doppler.

22. The method of claim 13, wherein the step of receiving real-time ultrasonic information comprises receiving tissue harmonic imaging information.

23. The method of claim 13, wherein the step of receiving real-time ultrasonic information comprises receiving pulse inversion harmonic imaging information.

24. The system of claim 1, further comprising a display displaying said portions of said adjacent image lines or planes within said rendering box processed by said volume rendering processor.

25. The system of claim 1, further comprising a display overlaying said portions of said adjacent image lines or planes within said rendering box processed by said volume rendering processor over said adjacent image lines or planes stored in said memory.

26. The method of claim 1, said rendering box control module further comprising an operator interface for modifying said thickness in real-time.

27. The method of claim 1, said rendering box control module defining a second thickness of said rendering box overlapping a portion of said adjacent image lines or planes, said volume rendering processor projecting said rendering box based on said second thickness onto portions of said adjacent image lines or planes in real-time while said ultrasound transducer continues to receive said real-time ultrasound information.

28. The method of claim 13, further comprising displaying volume rendered image lines or planes within said rendering box.

29. The method of claim 13, further comprising displaying a real-time image comprising volume rendered image lines or planes overlaying said adjacent image lines or planes.

30. The method of claim 13, further comprising defining a second thickness of said rendering box wherein said second thickness is different from said thickness, said projecting step projecting said rendering box based on said second thickness on said image lines or planes in real-time, said volume rendering step volume rendering said adjacent image lines or planes within said rendering box based on said second thickness.

31. A method for enhancing the contrast of a medical diagnostic ultrasound image, the method comprising:
defining a first thickness of real-time ultrasonic information;
acquiring a series of data slices comprising said real-time ultrasonic information within said first thickness;
projecting a rendering box onto each of said series of data slices;
volume rendering each of said series of data slices within said rendering box based on volume rendering techniques that enhance contrast; and displaying volume rendered data slices in real-time, said volume rendered data slices based on said series of data slices within said rendering box.

32. The method of claim 31, further comprising defining a second thickness of said real-time ultrasonic information, said acquiring step acquiring data slices comprising said real-time ultrasonic information within said second thickness.

* * * * *